(12) United States Patent
Wessel

(10) Patent No.: US 10,194,208 B2
(45) Date of Patent: Jan. 29, 2019

(54) TELEVISION ENABLED THERAPEUTIC COMMUNICATION SYSTEMS AND METHODS

(71) Applicant: Paul Wessel, Delano, MN (US)

(72) Inventor: Paul Wessel, Delano, MN (US)

(73) Assignee: FIRST LAYER HEALTH L.L.C., Delano, MN (US)

( * ) Notice: Subject to any disclaimer, the term of this patent is extended or adjusted under 35 U.S.C. 154(b) by 0 days.

(21) Appl. No.: 15/369,147

(22) Filed: Dec. 5, 2016

(65) Prior Publication Data

US 2017/0195739 A1 Jul. 6, 2017

Related U.S. Application Data

(63) Continuation of application No. 14/478,209, filed on Sep. 5, 2014, now abandoned.

(51) Int. Cl.
| | |
|---|---|
| *H04N 21/21* | (2011.01) |
| *H04N 21/488* | (2011.01) |
| *H04N 21/4367* | (2011.01) |
| *H04N 21/4788* | (2011.01) |
| *H04N 21/8352* | (2011.01) |
| *H04N 21/237* | (2011.01) |
| *H04N 21/6334* | (2011.01) |
| *H04N 21/258* | (2011.01) |

(Continued)

(52) U.S. Cl.
CPC ..... *H04N 21/4882* (2013.01); *G06F 19/3418* (2013.01); *G06Q 50/22* (2013.01); *H04N 21/237* (2013.01); *H04N 21/25816* (2013.01); *H04N 21/4367* (2013.01); *H04N 21/4788* (2013.01); *H04N 21/6334* (2013.01); *H04N 21/8352* (2013.01)

(58) Field of Classification Search
None
See application file for complete search history.

(56) References Cited

U.S. PATENT DOCUMENTS

| 7,185,282 B1 * | 2/2007 | Naidoo | A61B 5/0002 348/E7.071 |
|---|---|---|---|
| 2002/0129368 A1 | 9/2002 | Schlack et al. | |

(Continued)

OTHER PUBLICATIONS

Application and File history for U.S. Appl. No. 14/478,209, filed Sep. 5, 2014, Inventors: Wessel.

(Continued)

*Primary Examiner* — Cai Y Chen
(74) *Attorney, Agent, or Firm* — Patterson Thuente Pedersen, P.A.

(57) ABSTRACT

An apparatus, system and method for delivering messages to a television set includes the use of a health-related digital content messaging and compliance system (HDCMC) to facilitate communication between a medical provider, a digital television station and eventually the television set of an end user. The medical provider can place requests to the HDCMC to deliver requested health-related content to the television of the end user. The HDCMC transmits the requested health-related content to the digital television station, which in turn transmits the requested health-related content received from the HDCMC to the television of the end user using verification codes to ensure that the requested content is delivered to the intended television and/or viewer.

8 Claims, 14 Drawing Sheets

(51) Int. Cl.
  *G06Q 50/22* (2018.01)
  *G06F 19/00* (2018.01)

(56) References Cited

U.S. PATENT DOCUMENTS

2010/0153487 A1   6/2010   Greven et al.
2013/0125158 A1*  5/2013   Brown ................ A61B 5/0002
                                                725/14

OTHER PUBLICATIONS

Application and File history for U.S. Appl. No. 14/837,526, filed Aug. 27, 2016. Inventors: Wessel.
Jan. 1, 2016 USPTO Office Action (U.S. Appl. No. 14/478,209).
Nov. 2, 2016 USPTO Office Action (U.S. Appl. No. 14/837,526).
Jan. 5, 2016 USPTO Office Action (U.S. Appl. No. 14/478,209).
Newman, Jewish Home Lifecare named Innovator of the Year, McKnights, Haymarket Media, Inc., http://www.mcknights.com/jewish-home-lifecare-named-innovator-of-the-year/article/374286/, Sep. 30, 2014.
Spinsanta et al., Remote health monitoring for elderly through interactive television, BioMedical Engineering OnLine 2012, 11:54, http://biomedical-engineering-online.com/content/11/1/54, 1-18, Aug. 21, 2012.

* cited by examiner

TELEVISION ENABLED THERAPEUTIC COMMUNICATION SYSTEMS AND METHODS

CROSS-REFERENCE TO RELATED APPLICATIONS

The present application is a continuation application of, and claims priority to, U.S. application Ser. No. 14/478,209, entitled Television Enabled Therapeutic Communication Systems and Methods, filed on Sep. 5, 2014; the entire contents of which is incorporated herein by reference.

BACKGROUND

The 65-and older population will increase to 55 million in 2020 and by 2030 it is projected that this number will expand to 75 million. Nearly 75% of these older adults suffer from one or more chronic illnesses, requiring some manner of assistive care. Currently, these older adults are responsible for approximately 60% of the overall total healthcare expenditures in the United States and as the baby boomer generation migrates towards retirement this population will expand to over 108 million people over the next 15 years and the projected cost to the healthcare system is staggering if not unsustainable.

The largest group responsible for managing this increasingly fragile population is a concerned family member or close relative; 30% of these adult caregivers sacrifice wages and benefits to assist in the care of their aging loved one. It is also estimated that U.S. employers lose approximately $33.6 billion a year due to worker absenteeism due to caring for an older relative.

The increasing challenges of balancing cost, distance, and time commitment will motivate the concerned caregivers to find new technology-based solutions that will allow them to more closely monitor specific health and activities from afar, while allowing their loved ones to age within an environment that is most familiar and cost-effective.

The most common method of providing technology based distance care giving is generally referred to as home health monitoring. Typically, home health monitoring systems include a number of sensors and small computing devices, installed throughout a home that measure and report different activity levels of an individual. Most of these home health monitoring systems have been built on a wireless platform; requiring the resident to purchase and maintain an Internet broadband connection. The current broadband adoption rate of people over 70 years of age is less than 25% however, while the adoption rate of digital broadcast, cable or satellite television is nearly 100% within this same cohort; clearly indicating a technology disconnect with Internet-based devices and systems and preference for those technologies, i.e. the television set or monitor with which they are more accustomed.

According to Nielsen ratings, the average person over 65 years of age watches on average, 48 hours of television per week and according to the National Association of Broadcasters, there are over 45 million people that regularly view free broadcast television.

As its name implies broadcast television only sends it audio and video signals outward and does not possess the ability to receive any type digital feedback information back from its viewer.

Prior to June 2009, the broadcast television signal was analog and required some type of antenna to capture and direct the broadcast television signal into the television set.

In 1996, Congress authorized the distribution of an additional broadcast channel to every full-power TV station so that each station could launch a digital broadcast channel while simultaneously continuing analog broadcasting. Jun. 12, 2015 has been established as the target deadline for full power television stations to stop broadcasting analog signals.

Several important benefits were realized as part of this switch to all-digital broadcasting. Specifically, parts of the valuable broadcast spectrum have been freed up for public safety communications by groups such as police, fire departments and rescue squads, while still providing free television viewing channels to its customers. Additionally, some of the remaining spectrum has been auctioned to companies that are working to provide consumers with advanced wireless services, such as wireless broadband.

The migration from analog to digital television (DTV) has transformed the free television viewing experience. Instead of relying on the "rabbit ears" and aluminum foil antennas, viewers utilize signal conversion devices (such as for example: a digital broadcast set top converter box (DBSTCB) or in the case of digital cable and satellite programming a digital television set top box (DTSTB)), to processes the broadcast digital television signal from the television station and convert it back to an audio and video signal compatible with older television sets (Note: when discussing the functionality of DBSTCB and DTSTB systems herein it should be understood that newer television sets or monitors may incorporate such systems internally and that as such the present disclosure is not limited merely to the use of external signal conversion boxes, but includes the use of television sets or monitors (televisions) that incorporate such devices internally as well). This enables broadcasters to still offer the same free television viewing; now with enhanced picture and sound quality, and the ability to provide multiple channels of free viewable content.

Digital Cable and Satellite Television

Digital Cable and Satellite Television systems send their information through a DTSTB but there are several key distinctions when comparing this device to the DBSTCB; no analog to digital signal conversion is required, and immediate, bidirectional communication with the television viewer is established.

At the epicenter of digital broadcast, cable and satellite television systems are sophisticated software programs known as content management systems (CMS); whose primary tasks are to correctly identify and deliver specific pieces of digital entertainment programming content to a specific viewer(s). With digital broadcast television the number of channels to be managed is significantly less than cable or satellite television. Within cable and satellite television, local free broadcast television channels are still offered, such as educational channels from local colleges, and community access channels devoted to local governments (PEG channels) but are usually integrated into cable or satellite television's CMS program, so that all channels, whether paid for or free, are controlled by one system.

CMS incorporates other feature sets, including the ability to design and change program schedules, advertisements, and electronically interfacing with the television station's financial billing systems.

Many CMS packages allow limited outside customization of their standard product offerings to accommodate different viewership content needs and schedules. A software development kit (SDK) is a programming tool, developed by the CMS manufacturer that allows unique programming tasks or specific user interface development to be developed but outside this development layer key operational functions remain which assures that newly developed content operates like any other standard program function utilized on the CMS platform.

Common SDK development practices and guidelines typically require completion of a software approval process instituted by the CMS manufacturer for newly created content before approval is granted.

Underneath the CMS software's development and operational layers, resides the ability to conduct various levels of viewer data analysis: individual viewing patterns, types (free or purchased), genres, play times, duration of content play, and even channel surfing frequencies. CMS's analytical capabilities are designed for gaining a better insight into consumer viewing behavior which provides a foundation for building, modifying and delivering more user-directed content; which in turn, leads to higher customer retention, and profitability.

SUMMARY

It is a goal of the present disclosure to describe systems and methods which use and/or supplement the existing and evolving DTV infrastructure via their DBSTCB to provide viewers with secure, personalized communications in order to help the viewer achieve better health related outcomes regardless of the free television channel being viewed at the time. In addition, systems and methods of the present disclosure also have applicability to more sophisticated digital television signal delivery, namely cable and satellite television through the use of DTSTB, which allows for the possibility of bidirectional communications between potential healthcare providers (or their proxies) and viewers.

Note: while DBSTCB and DTSTB systems are presently external to most televisions (i.e. "set top"), within this disclosure it should be recognized and understood that the functionality of either device may be integral to a television, monitor or other viewing device (hereinafter collectively referred to as television sets) or be a part of a device external to the television set. In either circumstance, the term television set should be understood as including the functionality of the DBSTCB and/or DTSTB therein.

The systems and methods disclosed herein which rely on cable and satellite delivery of digital programming may be configured to utilize CMS analytical data sets to allow providers to customize and deliver potentially unique digital health-related content based on the interaction of the viewer through the bidirectional communication enabled by the DTSTB. In addition, by receiving immediate feedback from the viewer, important indications of compliance to and comprehension of the health related digital content being presented can by recognized by providers and thus subsequently deliver uniquely tailored programming, messages or services.

In addition to healthcare related messages and/or interactions, the systems and methods described herein may also be used to provide customized therapies or audio/visual experience based on the needs and/or desires of the viewer. For example, in the case of a viewer suffering from memory loss such as may be associated with conditions such as Alzheimer's and Dementia, the use of digital reminiscence therapy content such as audio/visual content that may be associated with the viewer's early years (such as favorites holiday songs, spirituals, hymns, children singing, religious readings, etc.) may not only provide valuable medical insight into an individual who is steadily migrating towards a nonverbal state, but may also serve as a method of alleviating high levels of anxiety or agitation and possible replacement of drug therapies.

Further method extensions of delivering digital health-related content through the television set have not only the created ability to receive information back from the viewer but to prioritize the healthcare provider's subsequent programming or service options based on the criticality and understanding of the subject matter by the viewer as reported in real time.

As age increases, cognitive function declines. The systems and methods described herein also provide unique methods of regularly sharing and updating information to an outside network concerned about the present status of viewer's cognitive, comprehension, functioning so that health care professionals, insurers and family members can refine digital health-related content to accommodate the individual's declining physical and mental state.

As more longitudinal data is gathered from the system other new data sets would become available that measure the effectiveness of digital health-related content in terms of both short and long-term health outcomes, speed of rehabilitation, compliance to medication and therapy regimens as well as measure the direct and indirect impact on health-care costs and quality of life.

In summary, delivery of digital health-related content to an individual through cable and satellite television's DTSTB present multiple methods of informing and gaining better insight into a viewer's cognition, comprehension, and compliance which can lead to delivering individualized digital health-related content that improve health outcomes and quality of life.

It should also be noted that of the systems and methods described herein, delivery of customized programming to viewers televisions through DTSTB enabled systems (via digital cable or satellite) or through DBSTCB enabled systems (via over the air digital programming) is achieved without the need of internet access on the viewer's part. While Internet-enabled home monitoring devices may be utilized with the systems and methods described herein, Internet connectivity is not necessary to enable a viewer to use or access the unique programming and message interactivity of the systems and methods disclosed.

In at least one embodiment, a system and method of its use comprises a system for delivering messages to a television set. Such a system includes a medical provider, a health-related digital content messaging and compliance system (HDCMC), a digital television station and at least one television set. In this system the medical provider is in communication with the HDCMC, the HDCMC is in communication with the digital television station, and the digital television station is in communication with the television set. When the medical provider places a request to the HDCMC to deliver requested health-related content to the at least one television set, the HDCMC is configured to transmit the requested health-related content to the digital television station. The digital television station is configured to transmit the requested health-related content received from the HDCMC to the at least one television set. The HDCMC provides the requested health-related content with a content digital address identification code. The at least one television set has a television digital address identification code. The requested health-related content is displayed on the at least one television set only when at least part of content digital address identification code matches the television address identification code.

In some embodiment a health-related digital content messaging and compliance system comprises a main processing element, a health-related content database, a specific health-related content request database, a patient personal medical information database, a communication interface with a medical provider, and a communication interface with a television station. In this embodiment the main processor is constructed and arranged to facilitate communication and access of the health-related content database, the specific health-related content request database, the patient personal medical information database by at least one of the medical provider and the television station.

These and other embodiments that characterize the disclosure are pointed out with particularity in the claims annexed hereto and forming a part hereof. However, for further understanding of the disclosure reference can be made to the drawings which form a further part hereof and the accompanying descriptive matter, in which there is illustrated and described embodiments of the disclosure.

DESCRIPTION OF THE DRAWINGS

A detailed description of the disclosure is hereafter described with specific reference being made to the drawings.

A detailed description of the disclosure is hereafter described with specific reference being made to the drawings.

DETAILED DESCRIPTION

Figure 1:
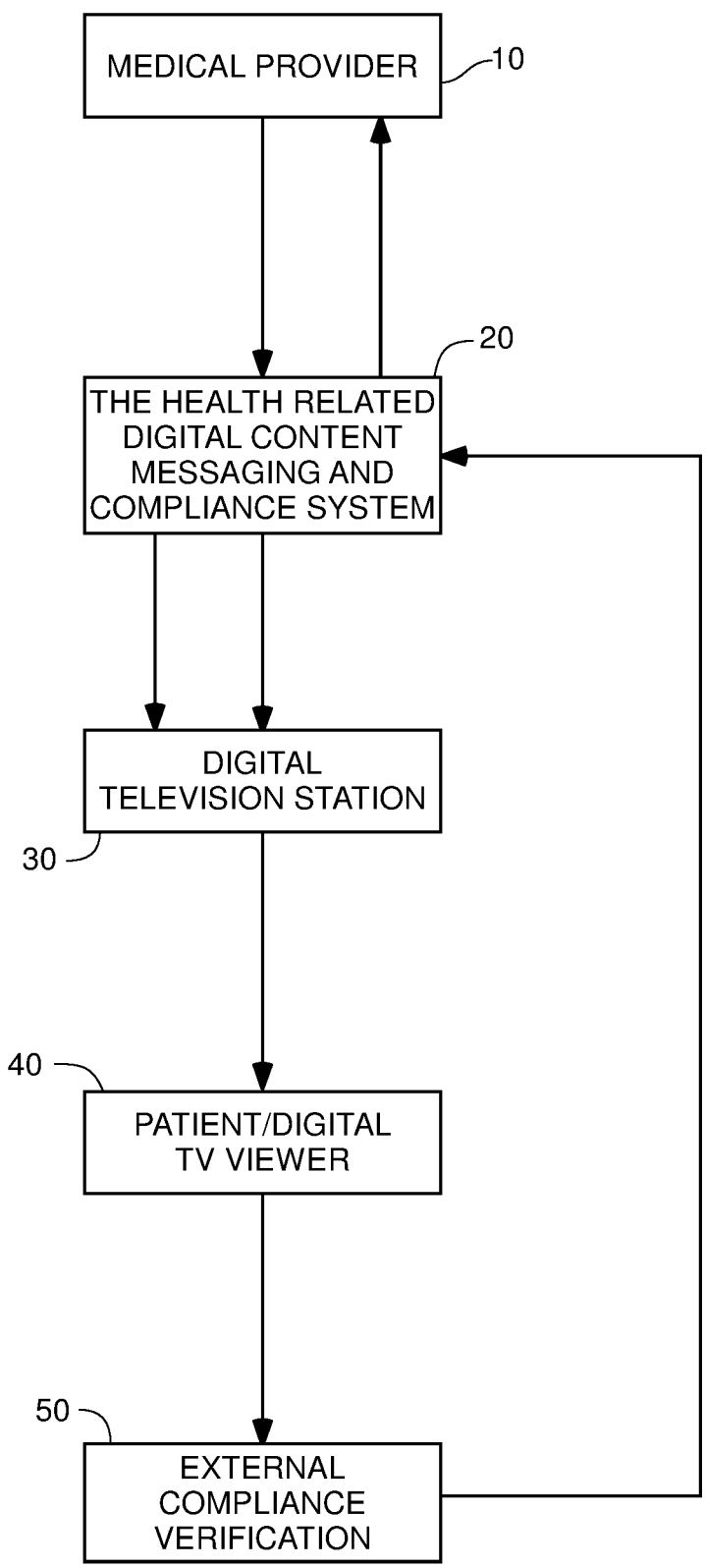
FIG. 1—Shows a block diagram of an embodiment of the disclosure comprising a digital television broadcast network.

While this disclosure may be embodied in many different forms, there are described in detail herein specific embodiments of the disclosure. This description is an exemplification of the principles of the disclosure and is not intended to limit the disclosure to the particular embodiments illustrated.

For the purposes of this disclosure, like reference numerals in the figures shall refer to like features unless otherwise indicated.

Figure 2:
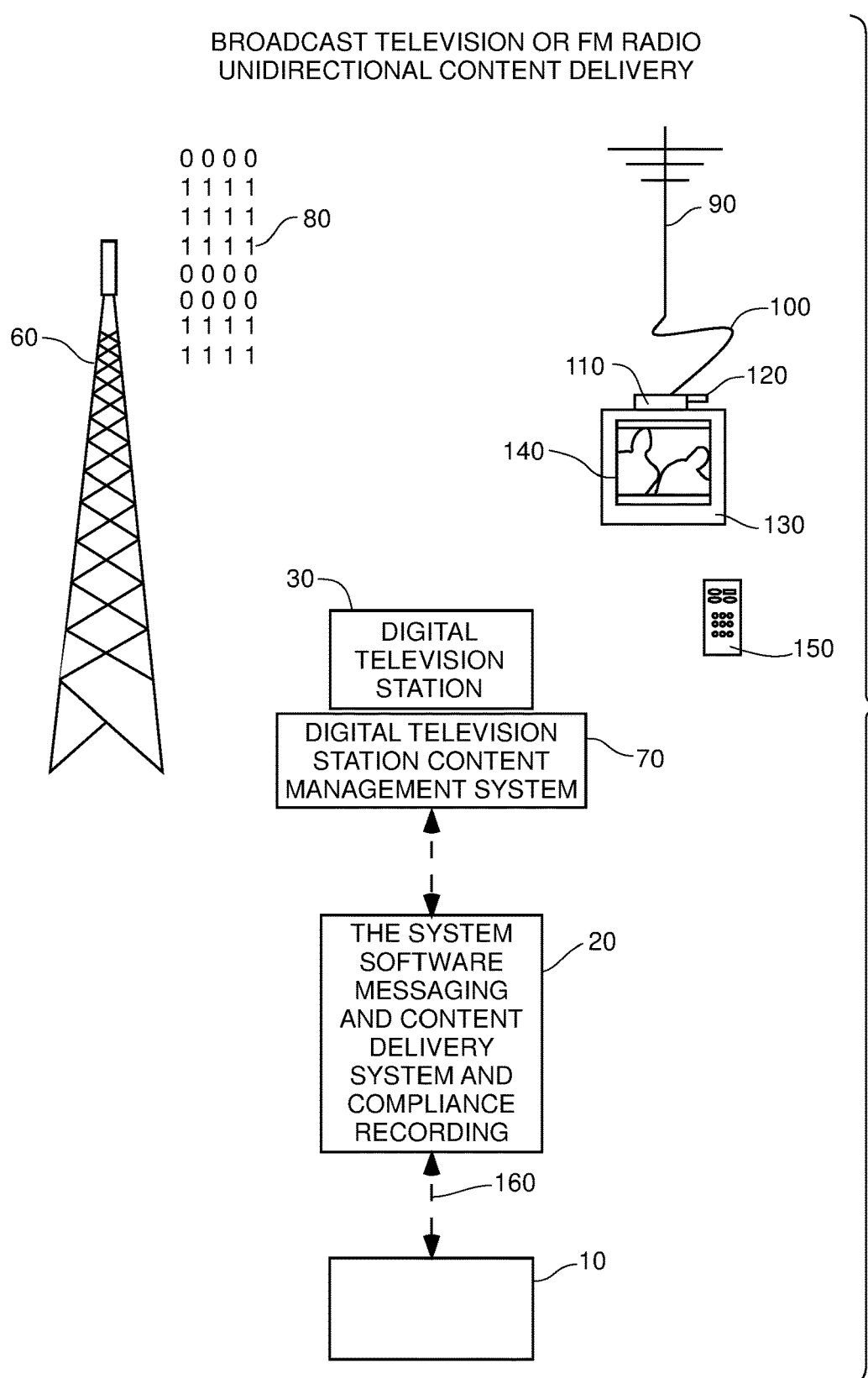
FIG. 2—Is an illustration of a broadcast television station transmission system as utilized by embodiments of the disclosure relying on DBSTCB.
Figure 3:
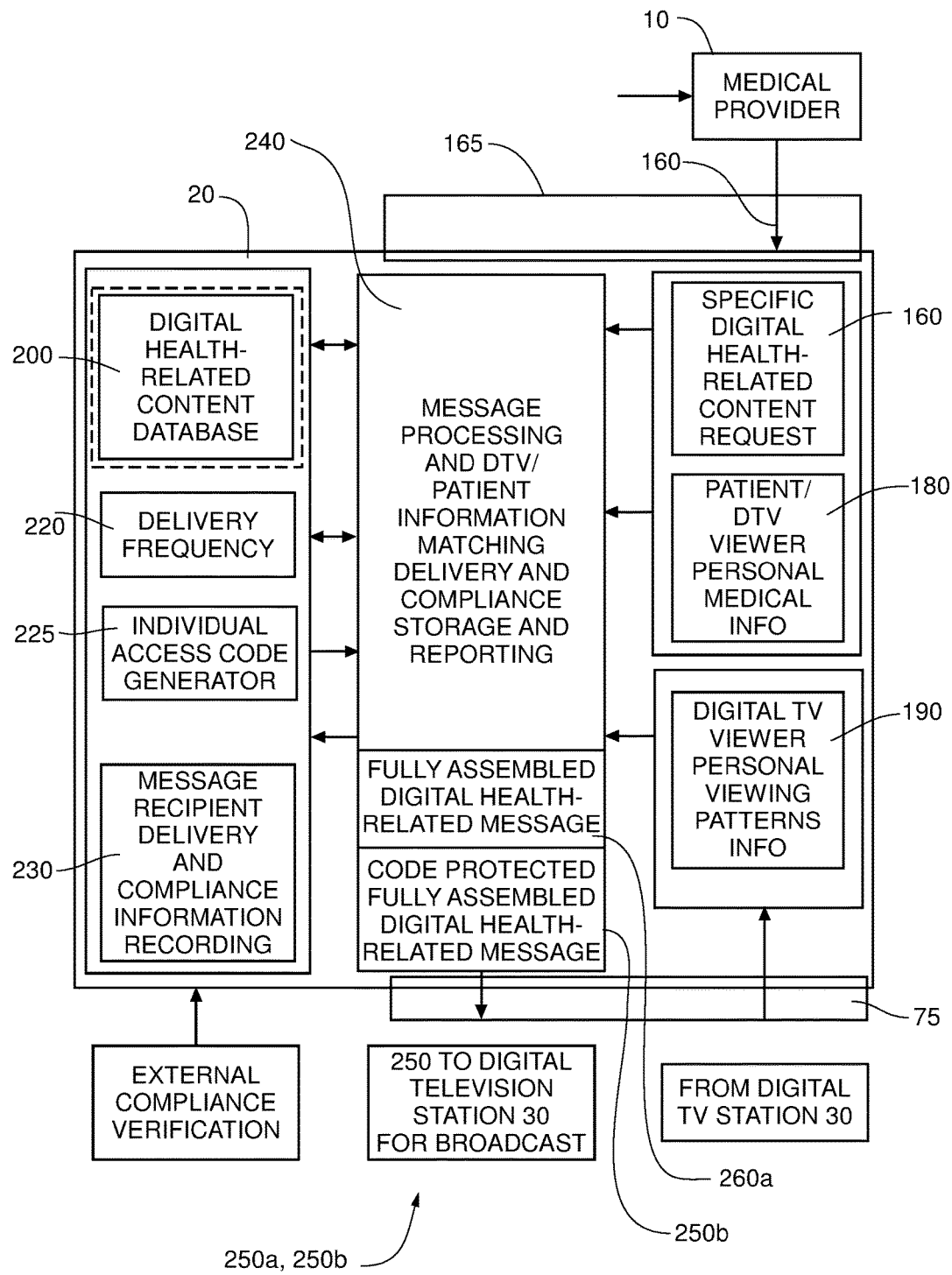
FIG. 3—Shows a block diagram of a system that distributes digital health-related content through a digital broadcast television network.
Figure 4:
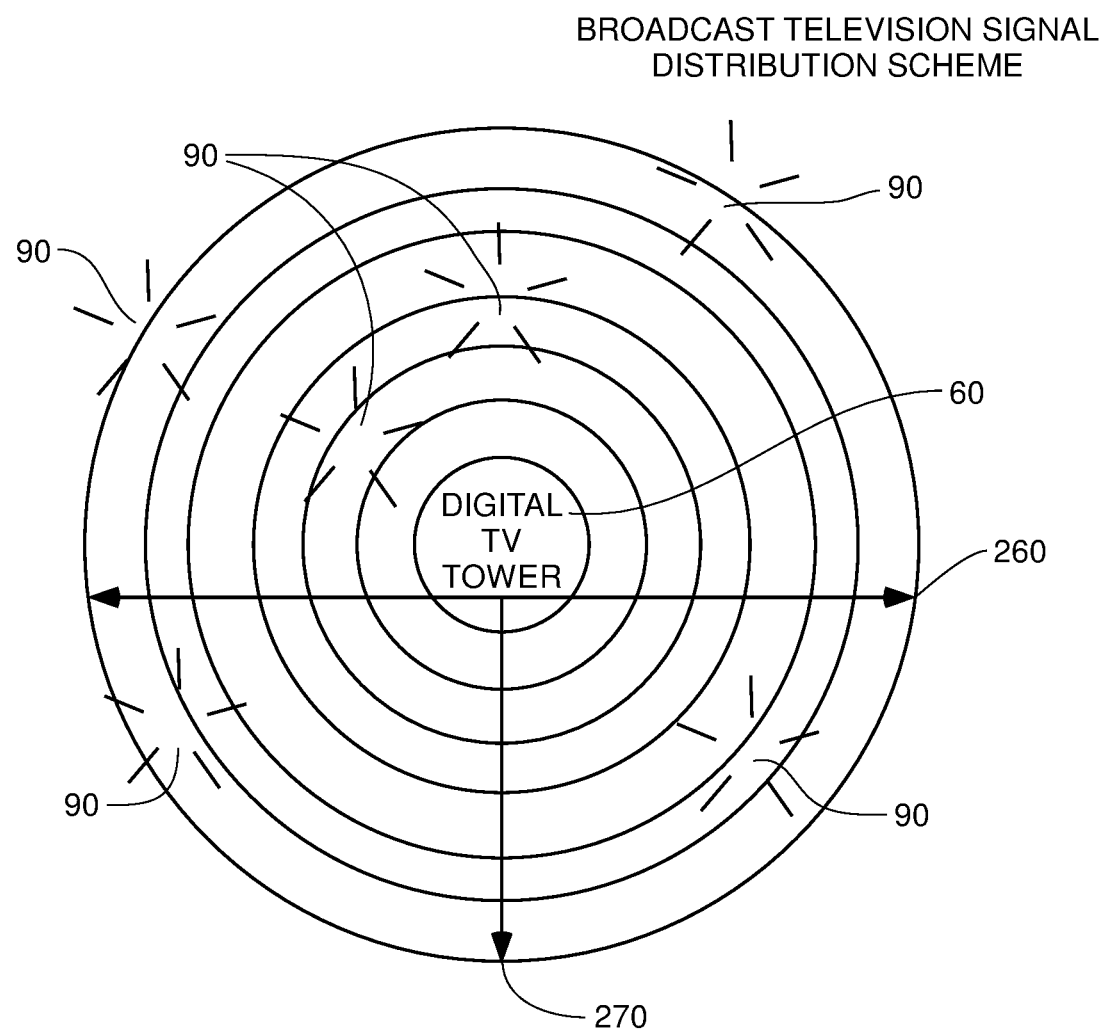
FIG. 4—Is an illustration of the broadcast range of digital broadcast television signal.

FIGS. 1-4 broadly represent components of a digital television broadcast system that distributes digital health-related content from a database of content 200 (such as is shown in FIG. 3) within a health-related digital content messaging system (HDCMC) 20, through a digital television broadcast network 260 (such as is shown in FIG. 4), while incorporating methods of verifying compliant activities and behaviors 50 of a patient/digital television viewer 40 in response to broadcasted and viewed digital health-related content.

As used herein "television station" refers to any digital television content provider and/or subscriber and delivery system such as a cable network or over the air broadcaster.

When a medical provider 10 issues a request 160 (see FIG. 3) to the system 20 (via communications interface 165) to deliver digital health-related content from the database 200 (see FIG. 3) to a patient/digital television viewer 40; the system 20 processes this request 160 and electronically exchanges specific patient/TV viewer 40 identification information 180, contained within the request 160 (see FIG. 3) and from the television station's 30 content management system 70 via communications interface 75. By matching the personal information 180 contained within the medical request 160, the main processing element of 240 can now properly identify, match coordinate, select and deliver digital health-related content from database 200 (see FIG. 3) to the intended patient/digital television viewer 40 via communications interface 75 with the digital television station 30.

External methods of verifying compliance behaviors 50 to viewing or hearing digital health-related content have also been incorporated into the system shown in FIG. 3, such as electronically receiving and recording completion of a required task contained as part of the digital health-related content, such as the digital health-related message instructing the appropriate patient/digital television viewer to pick up a prescription from a pharmacy and upon successfully completing this task. In such an instance of compliance 50, the pharmacy's point of sale system (not shown) electronically communicates to the system of 20, specifically through message recipient database 230 that the action has been completed. It is also contemplated that electronic receipt of external compliance information could be directly obtained from medical devices (not shown), such as a blood pressure blood glucose meters, mobile telephones and other computing devices involved in delivering certain aspects of healthcare to an individual.

As used herein the term medical provider 10 includes but is not limited to family members, insurers, spiritual organizations and other volunteers who participate in or are concerned about the medical, behavioral and emotional state of the patient/digital television viewer 40 and with their involvement could benefit from and participate in different elements cited within the context of this disclosure.

Figure 6:
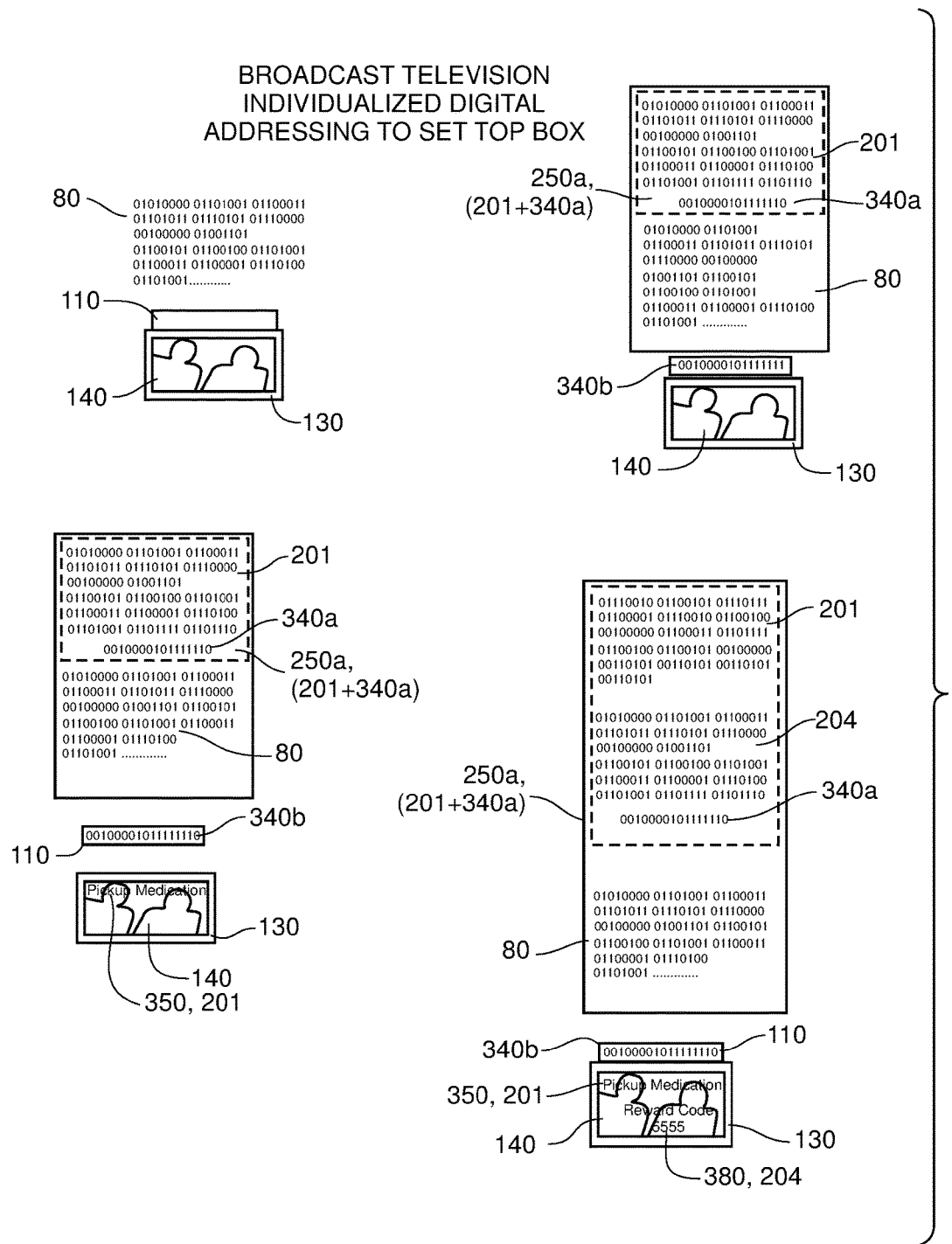
FIG. 6—Is an illustrative block diagram of how a digital health-related content is distributed and shown on a television set possessing a digital broadcast television converter box.
Figure 8:
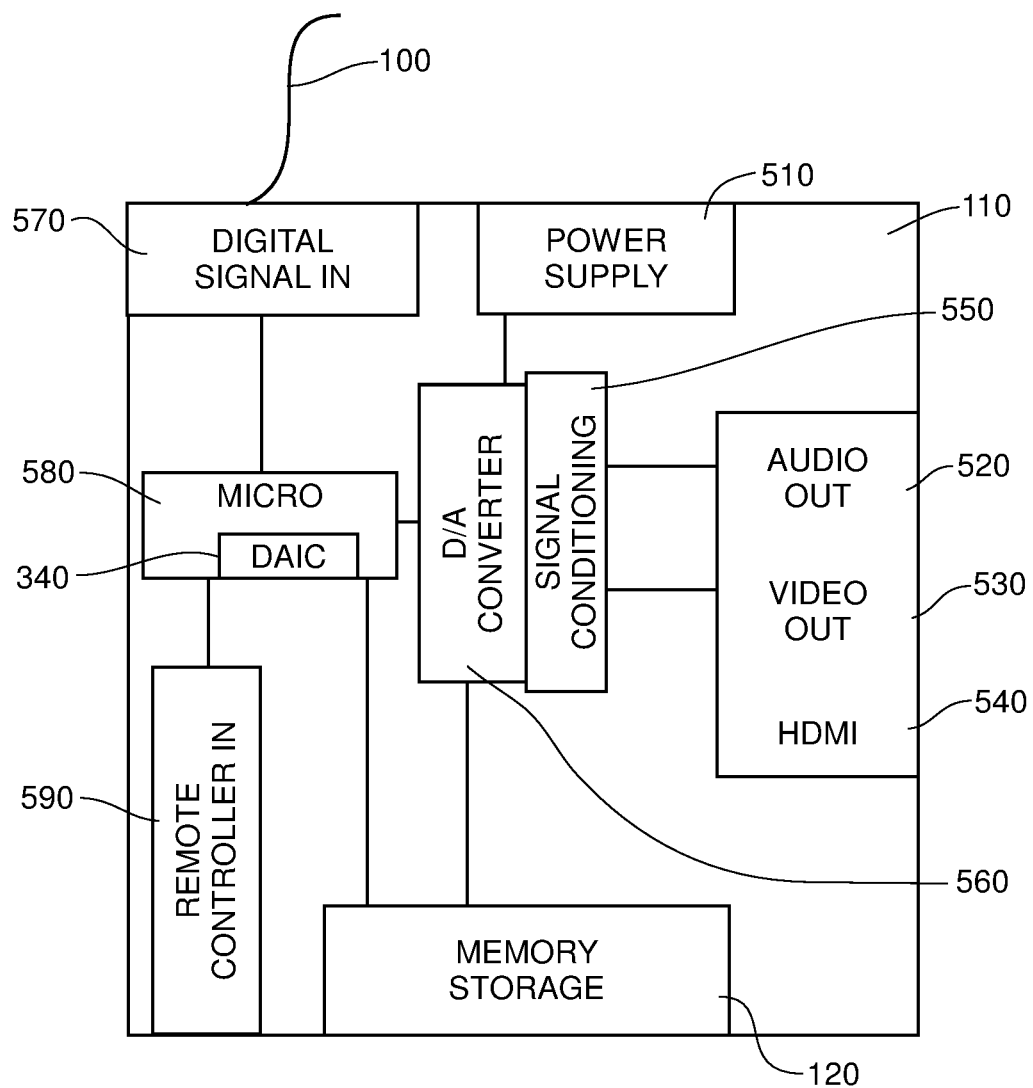
FIG. 8—Is an illustrative block diagram of the internal electronics of a digital broadcast set top converter box.

FIG. 2 broadly represents the operational aspects of broadcasting a digital television content signal 80. Wherein a television station 30 (see FIG. 1) has digital television broadcast capabilities to generate and broadcast a digital television content signal 80 through a digital television broadcast tower 60. Broadcasting a digital television content signal 80 is managed and coordinated by a digital television station 30 through a software system commonly referred to as a Content Management System (CMS) 70. The CMS 70 incorporates different operational aspects to properly manage the schedule and delivery of digital television content signal 80. The CMS 70 also contains a database of subscribers to the digital broadcast network 260 (see FIG. 4) that may also include registry of subscribers that have digital broadcast set top converter boxes (DBSTCB) 110 which are deployed throughout the broadcast network 260 (see FIG. 4). Each DBSTCB 110 contains a unique digital address identification code (UDAIC) 340b as illustrated in FIG. 6 and FIG. 8. The UDAIC is specifically used to target digital content delivery or wirelessly perform updates to the operational firmware within the DBSTCB 110.

In FIG. 2 it is also illustrated that the broadcast digital television content signal 80 is received by an antenna 90 (see also FIG. 4) that is operably connected to a DBSTCB 110 wherein the broadcast digital television content signal 80 is converted by the DBSTCB 110 into audio and video electronic signals 140 in operational compatibility with standard television set 130. The DBSTCB 110 also possesses a method of receiving instructions from a wireless remote control 150 for the DBSTCB 110 to perform other functions, i.e. save broadcast digital television content signals 80 into a memory storage unit 120.

Details of the system shown generally in FIG. 1 are provided in FIG. 3. Here it is shown that the system 20 provides the ability to electronically receive requests 160 from medical providers 10 that request delivery of specific digital health-related content 170 to a patient/digital television viewer 40 (see FIG. 1) who has the capability to view specific digital health-related content on a television set 130. The system 20 further incorporates a database of frequently used digital health-related content 200 that can be searched and matched with the specific digital health-related content requests 170 although additional methods for creating, uploading, and delivering unique or personalized digital health related messages are also provided for.

As shown in FIG. 3, the system 20 as herein represented, comprises several different elements in functional/electronic communication: the aforementioned digital health-related content database 200, a scheduling element or mechanism 220, the individual access code generator 225, the request 160 from the medical provider, the patient information 180, and the database 190 from which specific pieces of patient/digital television viewer 40 data is identified, extracted and assembled. The main information processing element 240 is responsible for coordinating these computing tasks, that when properly executed, produces a fully-assembled digital health related message 250a that is electronically sent to the digital television station 30 for broadcasting. Some specific medical requests 160 will insist that the delivery of digital health related content 250a meet HIPAA requirements that insure confidentiality of patient information, and content methods insure individual access to content. The system of 20, through its main processing element 240 in operable combination with individual access code generator 225 provides methods of generating and attaching an individual access code 225a to the delivery of the digital health related content 250a. When thusly secured by the addition of an access or security code 225a, the message 250a is depicted instead as message 250b.

Completing the system of 20 is a recipient compliance database 230 that receives electronically transmitted information from external sources and devices in the form of an external verification 50 that indicate compliance to certain management or compliance aspects contained within fully assembled messages 250a/250b. Finally, a method of reporting 255 external compliance verification 50 back to the medical provider 10 that the patient/digital television viewer 40 has received the message(s) 250a/250b can also be provided.

The health-related digital content database 200 assumes the existence and population of digital health related content already existing therein as provided by the medical provider 10 and/or viewer 40. In some embodiments, database 200 is configured for the receiving, creation and storages of personalized, customized, translated or other digital health related content types, such as personalized messages or videos from a medical provider or caregiver that might be beneficial to the patient/digital television viewer 40.

The system of 20, through the main processing element 240, incorporates the ability to electronically exchange and match personal identifying data sets (PIDS) of a patient/digital television viewer 40 (see FIG. 1), contained within the personal medical request 160 and information 180 and within the digital television's CMS 70 (illustrated in FIG. 2) for the purposes of correctly identifying the specific Digital Address Identification Code (DAIC) 340b (see FIGS. 6 and 8) of DBSTCB's 110 into which digital health-related content messages 250a/250b are to be delivered.

When the PIDS of personal medical information 180 contained within the specific digital health related medical request 160 and viewer subscribership information, containing the specific DAIC 340a address of patient/digital television viewer 40 found within the database 190 have been properly matched by the main information processing element 240, the correct Digital Address Identification Code (DAIC) 340b (see FIGS. 6 and 8) of DBSTCB's 110 (see FIG. 2) becomes located.

The main information processing element 240 within the system 20 then matches the specific digital health related content request 160 with the correct digital health-related content type contained within the digital content database of 200 with the requested delivery frequency contained within the scheduling element of 220. Once these steps have been executed by the main information processing element 240, a fully assembled digital health related message 250a/250b is formed and electronically sent to the digital television station's 30 content management system 70 where it is inserted and scheduled for delivery to the appropriate patient/TV viewer 40 (see FIG. 1).

Turning now to FIG. 4, here is provided an illustration of the approximate broadcast transmission range of a digital television content signal 80 (shown in FIG. 1) that can be detected by TV antenna's 90 or DBSTCB 110 (as illustrated in FIG. 3) located inside that coverage range.

Figure 5:
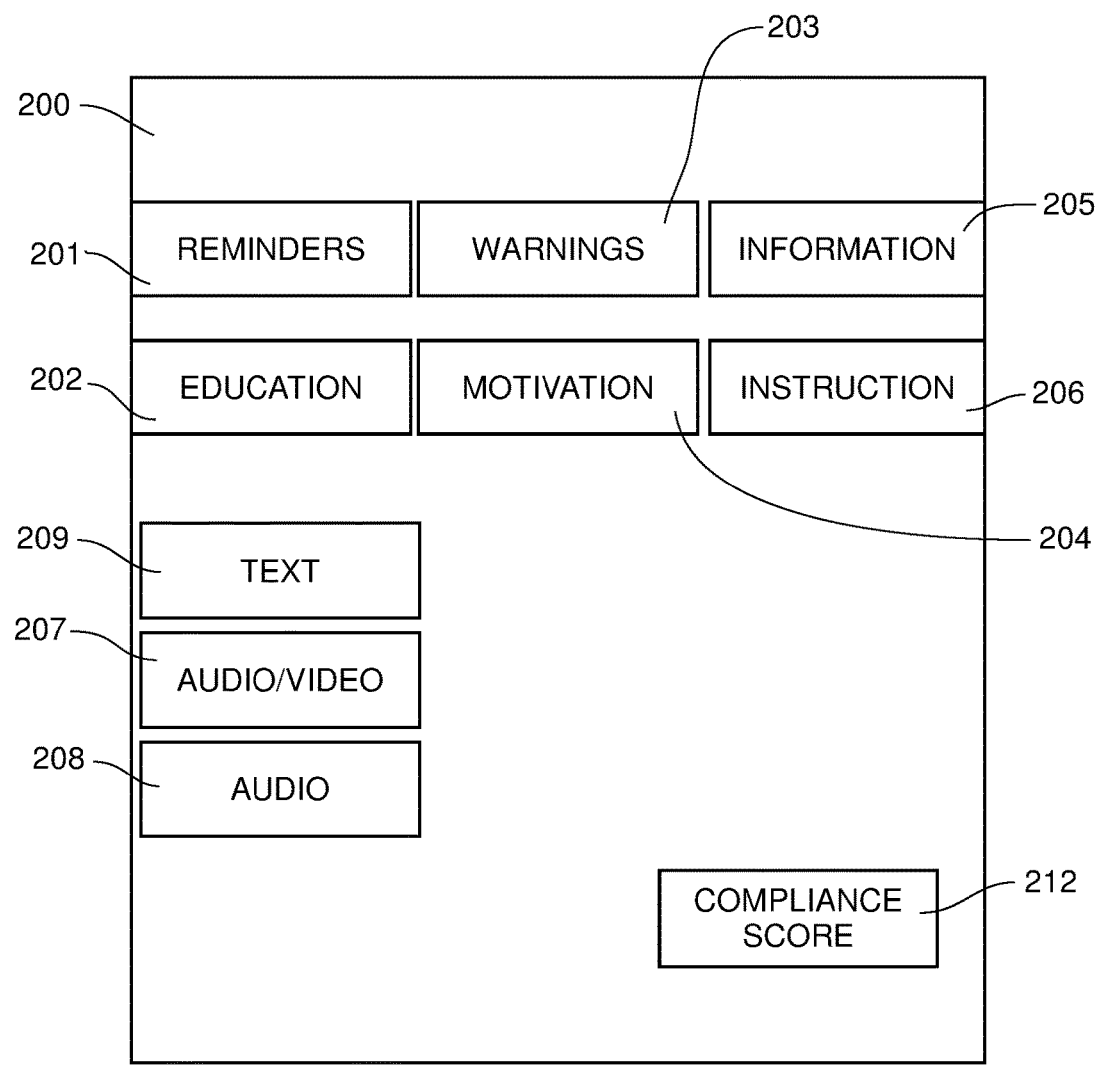
FIG. 5—Is an illustrative block diagram of the different types of digital health-related content that are to be distributed.

As shown in FIG. 5 a fully assembled digital message 250a/250b is assembled from a variety of possible media inputs contained within the Digital Health Related Content Database of 200, namely but not limited to Reminders 201, Education 202, Warnings 203, Motivation 204, Information 205, and Instructions 206. Another set of inputs within the Digital Health Related Content Database of 200 that is also selectable is the type of electronic format in which these messages types are to be delivered; namely Text 209, Audio 208, and Audio/Visual 207 (see FIG. 5).

Within system 20, developing and inserting a fully assembled specific digital health-related content message type 250a/250b is constrained by digital televisions' broadcast licensed spectrum availability. This places finite restrictions on the type, size and time of when digital health-related message type 250a/250b can be transmitted. Yet adequate broadcast spectrum currently exists within the broadcast of standard digital television content 80 to incorporate and deliver text message types 209 such as those illustrated in FIG. 5 that include but not limited to, Reminders 201, Education 202, Warnings 203, or Motivational Messages 204. It is also contemplated that text message type 209 could also be attached with an individual access code 225a from 225, resulting in a confidentially broadcasted digital health related message type.

Other embodiments within the Digital Health Related Content Database of 200 could contain different non health-related message types, such as a birthday or holiday greetings, that could be selected, conjoined, and delivered separately or in conjunction with the context of a fully assembled specific digital health related message 250a/250b that when delivered within a text format 209, could also be embedded into standard digital broadcast television delivery methods.

When delivered to the recipient television set 130, the message 250a/250b may be a unique transition consisting only of the message 250a/250b being sent from the television station 30 to the recipient(s) television set(s) 130; or may be a part of, or overlay, an existing transmission such that the message 250a/250b is eventually displayed concurrently (or from the viewer's perspective: "on top of") the television program which the viewer is currently viewing and/or listening to without undue interruption or significant interference with that program. For example, while watching the evening news, message 250a/250b can be sent to the television set 130 of a viewer 40 who may receive that message 250a/250b in the form of a scrolling text on the screen of their television set, or alternatively as an audio message only which momentarily is presented over the audio of the program, etc.

Information type 205 contains general health related message types that are non-specific in nature such as information on community health screenings and other health events. Compliance score 212 represents a simple message type output that has been created by the main processing element 240 from information electronically derived from the external compliance verification 50. In some embodiments, score 212 can be attached with any other digital health related content, contained within the digital health related content database of 200 to provide an outgoing measurement indicator to the patient/digital television viewer as to their compliance performance.

In some embodiments most message types will be delivered in a text format to optimize spectrum usage, accommodate viewer schedules or leverage digital broadcast content 80 viewing popularity to increase message receipt and enhance compliance, but it is further contemplated that any message type 201-206 could utilize any message format type 207-209 to achieve desired outcome from the delivery of the fully assembled digital health related content, 250a/250b.

In some embodiments modification to message types 207-209 could occur to increase awareness when being viewed. These modifications could include but are not limited, increased audio volume levels and color contract of audio/video message type 207 or increasing font size, color and speed of delivery of text message type 209.

By cross-referencing the patient/viewer data of databases 180 and 190 the medical provider 10 can modify the nature of the message 250a/250b to be displayed in a variety of ways. For example, if it is determined that the intended viewer 40 has a vision problem, the message font of a text type message 250a/250b may be modified so as to appear significantly larger on the display of the television set 130, and/or to include a corresponding audio form of the message 250a/250b. In this manner all aspects of the health-related message's display characteristics and mode of delivery can thus be customized to the needs of any specific patient.

Turning now to FIG. 6, an illustration is provided that depicts the delivery of a fully assembled specific digital health related message 250a/250b (see FIG. 3) in combination with a broadcasted digital television content signal 80 (see also FIG. 2).

As previously shown in FIG. 2, the broadcast digital television content signal 80 is sent from the digital television station 30 through its digital content management system 70 and received by a digital broadcast set top converter box 110 of the television set that converts the digital television content signal 80 to display a sound and/or image 140, representative of the digital television content signal 80, onto a television set 130. FIG. 6 depicts a digital representation of a fully assembled digital health related message 250a/250b, that contains a Reminder message type 201 in a text format 209 (see FIG. 5) accompanied with the unique (DAIC) digital address identification code 340a that properly corresponds to the digital address 340b contained within the electronics of the digital broadcast set top converter box DBSTCB 110.

When the broadcasted digital address identification code of 340a matches the digital address identification code 340b contained within the digital broadcast set top converter box DBSTCB 110, the digitized version of message 250a/250b containing message type 201, in text format 209, is allowed to be transmitted and converted by the digital broadcast set top converter box DBSTCB 110 resulting in a visually displayed message 350 onto the television set 130, along with the rest of the converted standard digital content signal 140.

When message 250a/250b containing message type 201 in text format 209 representing the embodiment of the fully assembled specific digital health related message 250a and the unique digital address identification code 340a is broadcast, and the digital address identification code 340b of the digital broadcast set top converter box 110 does not match, the message content is not downloaded.

Lastly, the ability to integrate fully assembled specific digital health related messages 250a/250b with other non-health-related message types are illustrated. The following example contains three specific parts: a non-health-related message type 204, a health-related message type 201 and the digital address identification code 340a corresponding to the digital broadcast set top converter box 110 to which it is delivered. Within the digital health-related content database 200, are different digital message types that can be accessed, utilized, and assembled to form a fully assembled specific digital health related message 250 (see also discussion of FIG. 5 above). Box 204 is a digital representation of a motivational message type selected from within 200 that has been integrated with a health related reminder message type 201 also contained within the database of digital health related content database of 200 along with the unique digital address identification code 340a which corresponds to the address of the digital broadcast set top converter box 110.

When the broadcasted digital address identification code of 340a matches the digital address code 340b of the converter box 110 the digitized version 250a/250b containing reminder message type 201 and motivational message type 204, in text format (see also FIG. 5) are converted by the digital broadcast set top converter box 110 and are now displayed as message images 350 and 380 on the television set 130.

Figure 7:
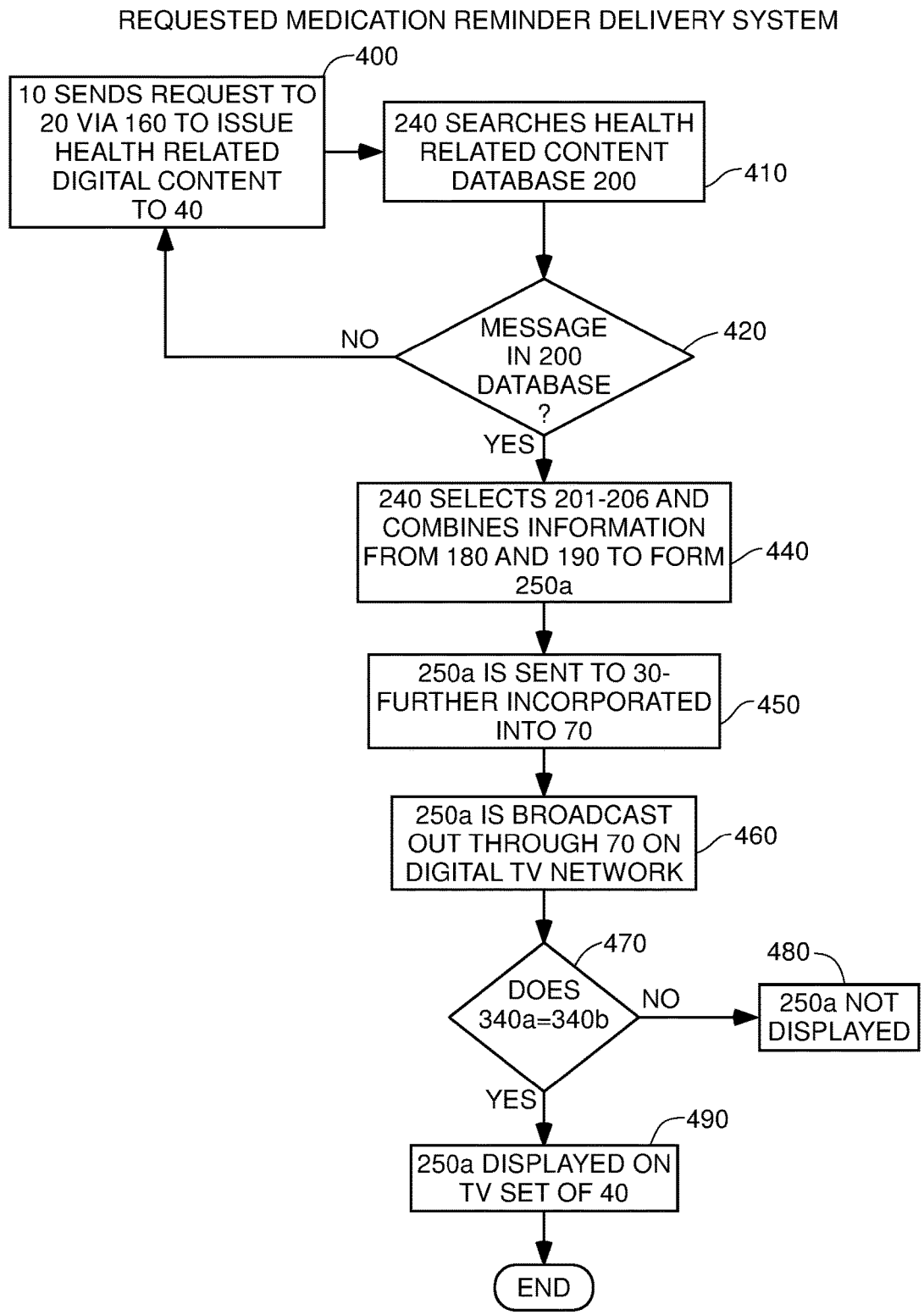
FIG. 7—Is a flowchart of how a medication pickup reminder constructed and delivered through a broadcast television network.

FIG. 7 illustrates a flowchart of depicting the system 20 processing a request 160 from a medical provider 10 to obtain a specific digital health related content from digital health-related content from database 200 such as previously discussed (see also FIGS. 3 and 5) and to send a full assembled digital health related message 250a/250b, in the form of reminder message type 201 from a medical provider 10.

In step 400, the system 20 receives an electronic request 160 from a medical provider 10 (such as a pharmacy for example) to issue a text based medication pickup reminder message 201 in text format 209 to a specific patient/TV viewer 40 (see FIG. 1). At step 410, the main processing element 240 searches for requested text message type 160, 201 against previously created digital reminder message types 201 previously stored within digital health related content database 200 (see FIG. 3). If the requested text message type 201 is found at blocks 420 and 440, the main processing element 240 uploads and attaches it with other processed personal patient/digital television viewer 40 information, most notably the DAIC 340b of the digital set top converter box 110 associated with the patient/digital television viewer information 180 and 190 to whom the requested message 160 is to be sent. DAIC 340a and message type 201 are combined by the main processing element of 240 to form a fully assembled digital health related message 250a/250b.

At step 460, the fully assembled digital health related message 250a/205b is electronically sent from the main processing element 240 to the content management system 70 (see FIG. 2) of the digital television station 30 that then coordinates and broadcasts delivery of the fully formed message type 250a/250b to the patient/TV viewer 40 (see FIG. 1).

At step 470 it is shown that when the fully assembled health related message 250a/250b is broadcast that digital address identification code 340a, contained within the fully assembled health related message 250a/250b must match the DAIC 340b of the digital set top converter box 110. When the DAIC 340a matches DAIC 340b within the digital set top converter box 110, the medication pickup message 201, in text format 209 is displayed as 350 on the television screen 140. As block 480 indicates, if no match is made with the DAIC codes 340a and 340b no medication pickup message 250 is displayed.

Turning now to FIG. 8, a block diagram is provided to illustrate the key operational components of a digital broadcast set top converter box 110 such as is shown in FIG. 2. Element 570 represents the physical input connection point into the digital set top converter box 110. Element 580 represents a micro controller or other executable firmware for instructing the digital signal to be converted via an analog to digital converter 560 and electronically filtered via a signal conditioner or filter 550 and sent to video and audio output points, 520, 530, and 540 in a compatible format that can be utilized by a standard television set 130 or saved to a memory storage location 120. The micro controller or other executable firmware can also receive operational instructions from a remote control 150 through its input 590 to perform functions of retrieving and playing digital content stored on 120.

A key feature within the digital broadcast set top converter box 110 is the storage of a digital address identification code 340b such as has been previously discussed (also see FIGS. 6 and 7). The digital address identification code 340b permits the digital television station 30 (see FIG. 1) through its digital content management system 70 (see FIG. 2) the capability of sending specific digital content signals 80 to a specific digital broadcast set top converter box 110. In many cases, executable software updates to the micro controller 580 and other firmware are performed this way.

Figure 9:
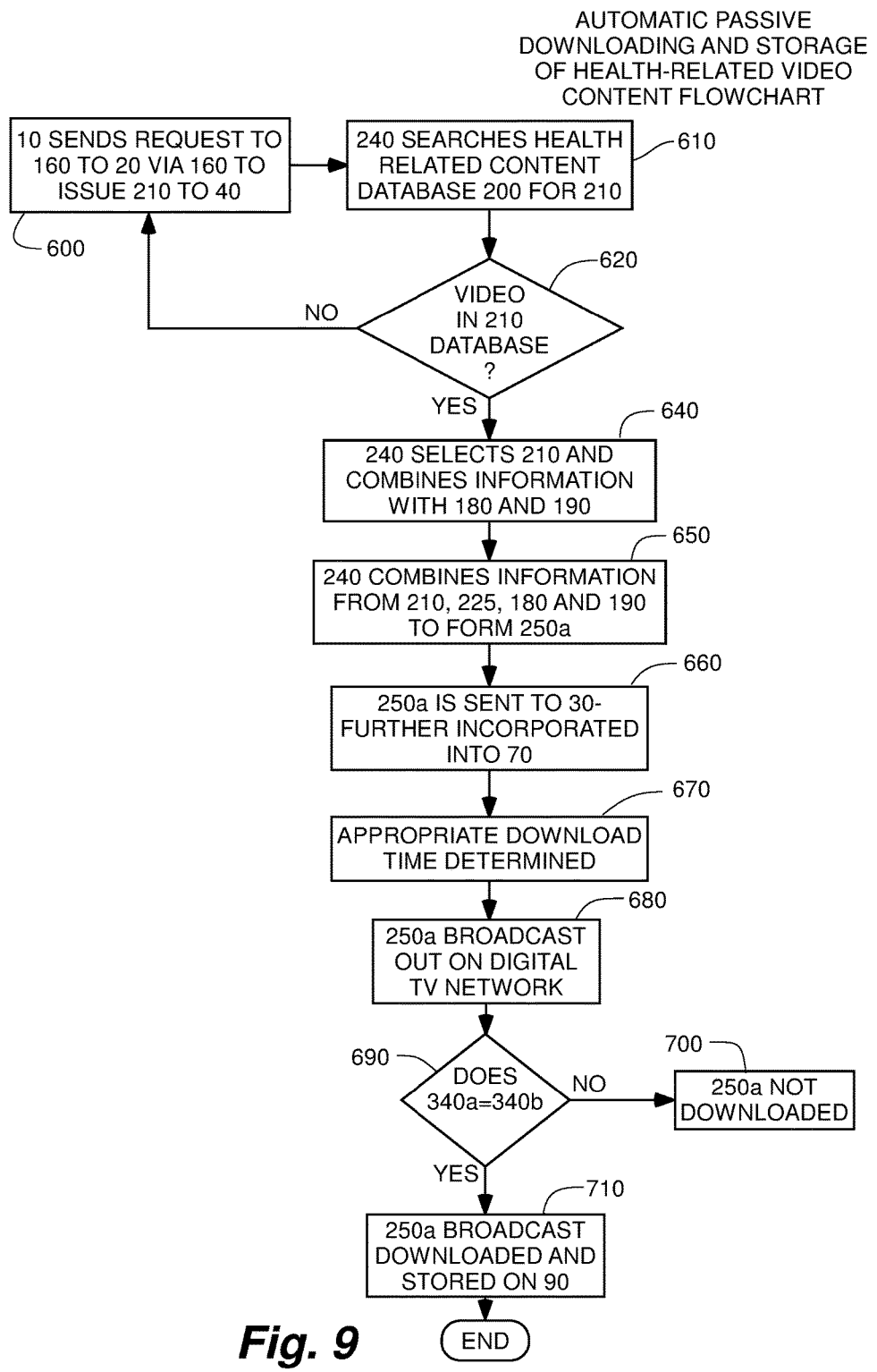
FIG. 9—Is a flowchart that illustrates the process of downloading and storing a health related video to a remote memory storage location.

FIG. 9 represents the process of delivering an instructional video 600 targeted to a specific digital set top converter box 110 (see FIG. 2) within the range of a digital television network 260 (see FIG. 4).

The process of delivering an Audio 208 or Audio/Video 207 message type is handled differently, due to the amount of data required when compared to text message types 209. The process for identifying, matching and assembling health related message types with the specific address 340b of the digital television set top converter box FIG. 2, 110 of the intended patient/digital television viewer 40, steps 600-650 are the same as those found in FIG. 7 400-450. However delivery and storage of any health-related video, FIG. 5, 207, 208 should be scheduled 670 and delivered by the station 30 during off-peak viewing hours so that the entirety of the network's digital television spectrum is not consumed.

At step 470, upon receipt of the matching digital address identification 340a/340b codes such as are shown in executable firmware within the micro controller 580 of the digital television set top converter box 110 (see FIG. 2) can direct the storage for the instructional video content 207, 208 to be directly saved within its memory storage unit 120 (see FIG. 1).

Once the instructional video had been downloaded, the viewer could be informed through a simple message delivery, similar to the delivery of the health-related message type in FIG. 6, 350 could be constructed informing the patient/TV viewer FIG. 1, 40 that instructional video had been downloaded into their digital television set top converter box and awaits retrieval and viewing.

In FIG. 9 a program decision tree is illustrated which includes the ability for the main processing element 240 to generate, assign, and integrate individualized access code 225a to view health-related digital video content 210, extracted from the health related digital content database 200 and in operable electronic communication with 225, both elements being contained within the system of 20. Attaching a personal access code 225a (IVAC) insures higher levels of confidentiality and privacy for the patient/digital television viewer 40.

It is contemplated that entering the personal access code 225a (which functions to provide an additional layer of security and confidentiality over and above the use of automatic codes 340a and 340b) and unlocking secure health related digital content would be accomplished through the electronic television remote controller 150 that is in operable combination with the digital set top control box 110. Although video content is shown here as the example embodiment for securing delivering of health related digital content, the same processes above described could also be used to unlock digital health related content in text or audio format.

Upon receiving notification that a digital health-related content 200 had been delivered the patient/TV viewer, 40 could be instructed to enter via remote control 150 (see FIG. 2) a specific access code 225a (see FIG. 3) which had been previously assigned and obtained.

Figure 10:
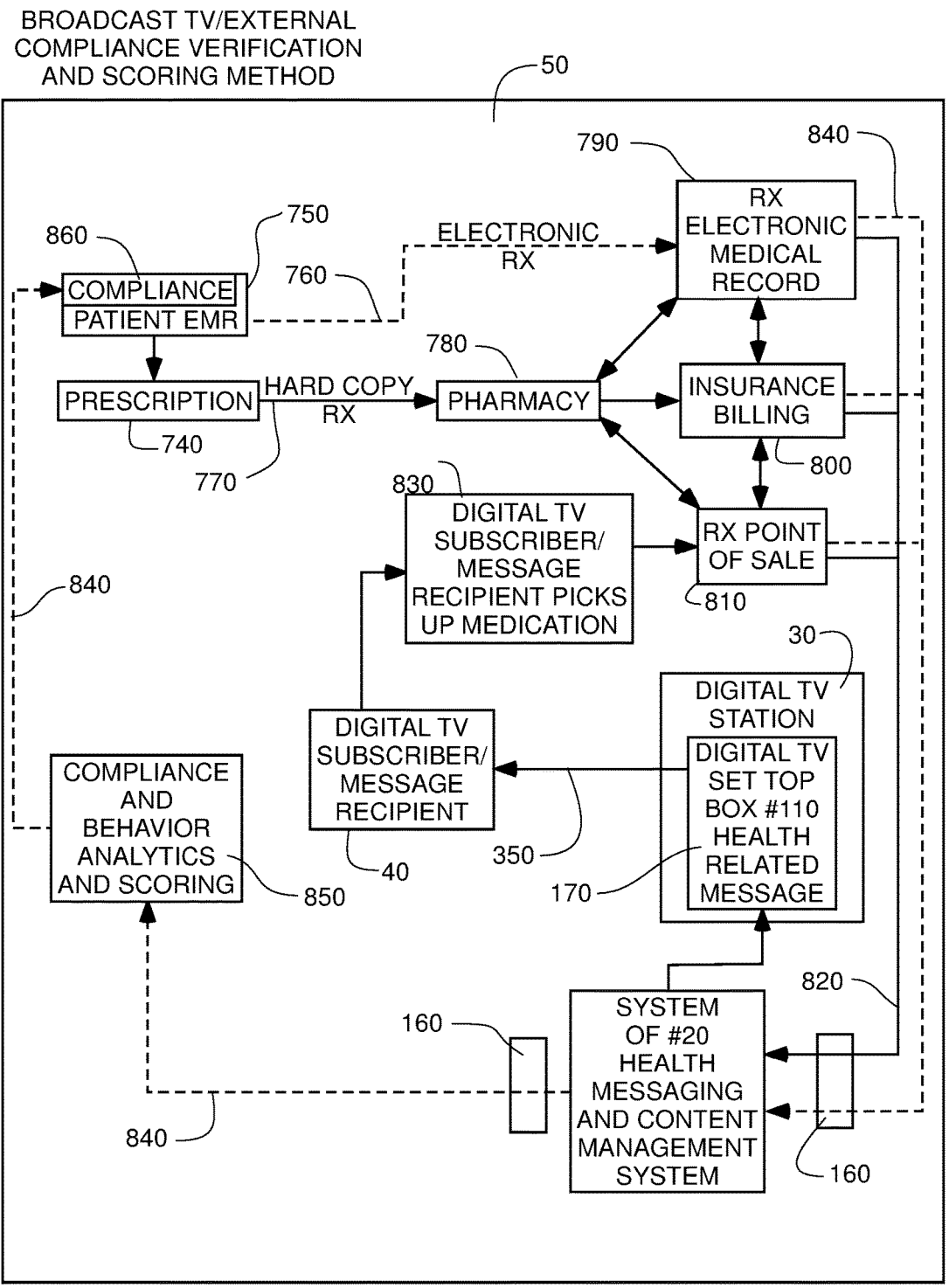
FIG. 10—Is an illustrative block diagram of externally measuring compliance to a digitally broadcast, health-related message type.

FIG. 10 illustrates another aspect of the system of 20 (see FIG. 1) that incorporates verifying compliance to a particular health-related digital content 50 by further developing compliance measurement metrics and feedback 840 to a medical provider 10 through issuance of a compliance reference score 860. This information is returned to a medical provider 10 and electronically stored within the patient/digital television viewer's 40 electronic medical record 750, which provides an on-going indication to the medical provider 10 of the patient's comprehension and response to health-related message types and delivery formats.

In the embodiment shown, a prescription 740 being generated manually 770 or electronically 760 by a medical provider 10 (see FIG. 1) that is delivered to a pharmacy 780. Upon receipt, prescription 740 or 770 is inputted into the pharmacy's prescription management system 790. The pharmacy's prescription management system 790 is in operable electronic communication with an insurance billing system 800 and the pharmacy's Point of Sale (POS) system 810.

Upon processing prescription information, the pharmacy's prescription management system 790 determines a time for the patient/digital television viewer 40 to return to the pharmacy and obtain the prescription 740. The pharmacy's prescription management system 790, is in operable communication (see arrow 160 in FIG. 3) with the system of 20 (see FIG. 1), which electronically sends a digital health related message request 170 (see FIG. 3) for to inform the patient/digital television viewer 40 (see FIG. 1) that a prescription awaits pickup at the physical pharmacy locale.

Upon receipt of the digital health related message 25a/250b (see FIG. 3) the patient/digital television viewer 40 (see FIG. 1) responds by going to the pharmacy location and picking up the medication, which can act as a verification 170. For example, within the process of picking up the medication, an electronic business transaction occurs with through the pharmacy's electronic point of sale system 810 in operable electronic communication with the pharmacy's prescription management system 790 that is in further operable electronic communication with the insurer's billing system. Once this medication pickup transaction has been completed by patient/digital television viewer 40 the system of 20, in operable electronic communication with 790, 800, 810, or any combination thereof is informed and the patient/digital television viewer's message delivery database 230 is updated.

Upon electronic notification that a compliant action by the patient/digital television viewer had been externally verified 50, i.e. picking up a medication at the pharmacy, the system of 20, through the main processing element 240 electronically scores the timeframe from which the health related message type 250a/250b (see FIG. 3) was issued until the compliant action had been externally verified 50. This compliance score is electronically sent from the system of 20 through 255 (see FIG. 3) to the medical provider 10 and updates the patient/digital television viewer's 40 electronic medical record 750.

Figure 11:
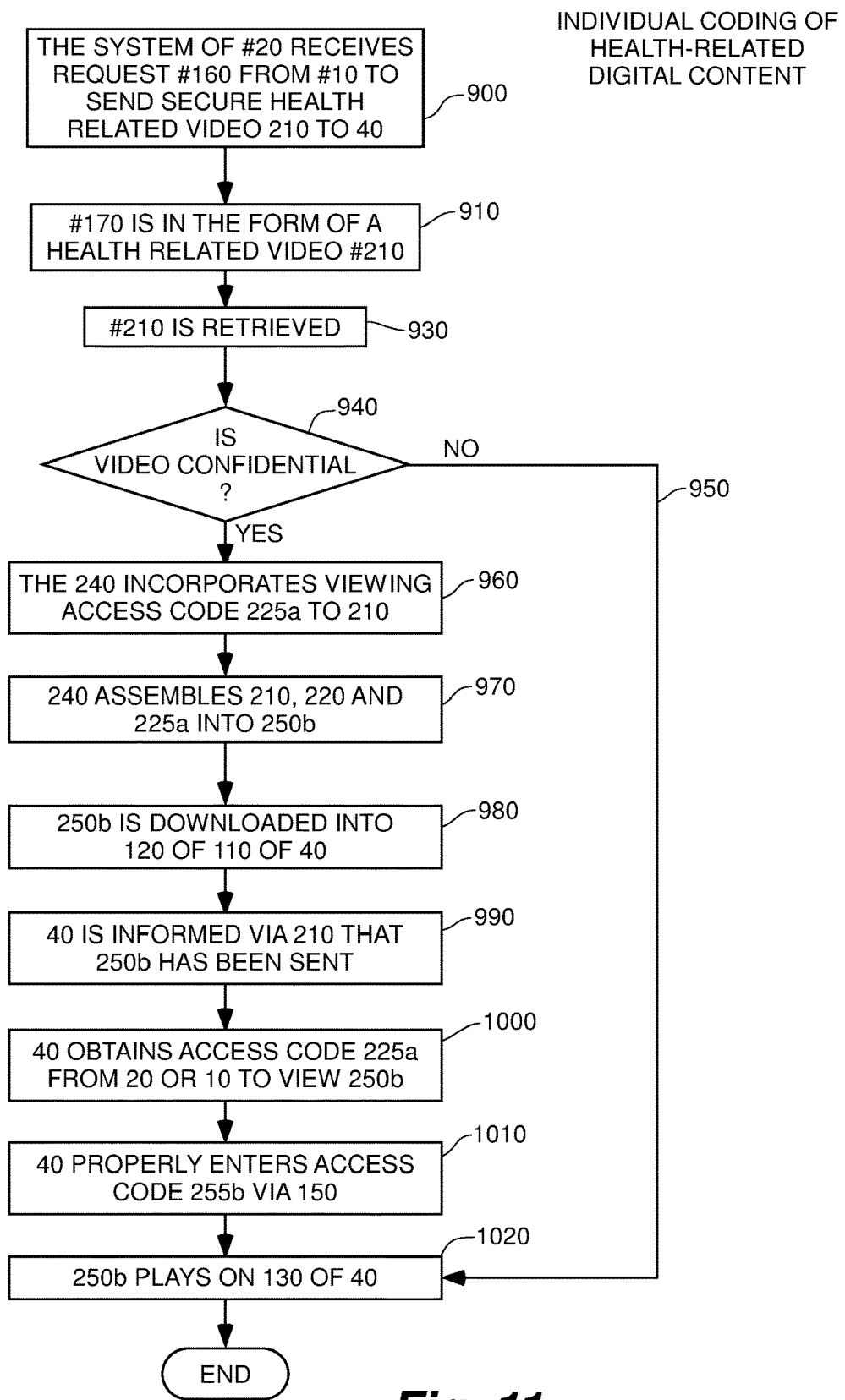
FIG. 11—Is a flowchart that illustrates the providing access coding to digital health-related content.

Delivery of health related information that may include confidential information intended to be viewed by an individual living within a residence utilizing a digital broadcast, cable or satellite television system. FIG. 11 describes a method for generating, incorporating, and issuing a confidential access code that locks and unlocks viewing of the health related video until the access code is entered.

At step block 900, the system 20 receives a request 170 to send a health related digital content to a patient/digital television viewer 40 (see FIG. 1). At step 910, the request to send health related digital content is in the form of a health related video 210. The system 20 performs a search of all existing health related videos 210 within its database. If the health related video 210 is found within the database it is retrieved at step 930 by system 20. At step 940 the video 210 is reviewed to determine if any content is confidential to a specific viewer in a household by the medical provider 10 (see FIG. 1).

At step 960 an additional method of creating and attaching a viewing access code 225a to the health related video 210 are performed by 240. In step 970, processor 240 assembles the health related video content 210 with the appropriate delivery schedule/frequency 220 (see FIG. 3) and individual viewing access code (IVAC) 225a to form a fully assembled, confidential health related digital content package 250b that awaits insertion into the broadcast, cable or satellite television's CMS 70 (see FIG. 2).

Proceeding to step 980 of FIG. 11, in the case of broadcast digital television the fully assembled secure digital health-related content 250b is downloaded into memory storage 120 of the DBSTCB 110 (see FIG. 2). In the case of cable and satellite television, secure content 250b is stored within the CMS 70, patient/TV viewer is electronically notified that a confidential health related video file awaits access or download (see FIG. 2). In 1000 the patient/digital television viewer 40 receives or had received the proper IVAC that provides access to view or listen to the fully assembled secure digital health-related content 250b. FIG. 11 illustrates that the main processing element of 240 is responsible for generating and attaching the individual access code 225a to the appropriate digital content 200, although other methods of externally providing the IVAC of 225a to the system of 20 are herein contemplated, such as utilizing the patient/digital television viewer's 40 medical identification number, social security number, driver's license number or medical insurance number. Upon receipt of the IVAC 225a, the patient/digital television viewer 40 enters the assigned IVAC 225a with the digital set top box remote control unit 150 that is operable, electronic communication with the digital set top box 110. Upon successful entering of the IVAC 225a, the patient/digital television viewer is granted access to view fully assembled secure digital health-related content 250b. Other methods of providing and verifying individual access to fully assembled secure digital health-related content 250b are also herein contemplated such as utilization of a finger print or retinal scan.

Figure 12:
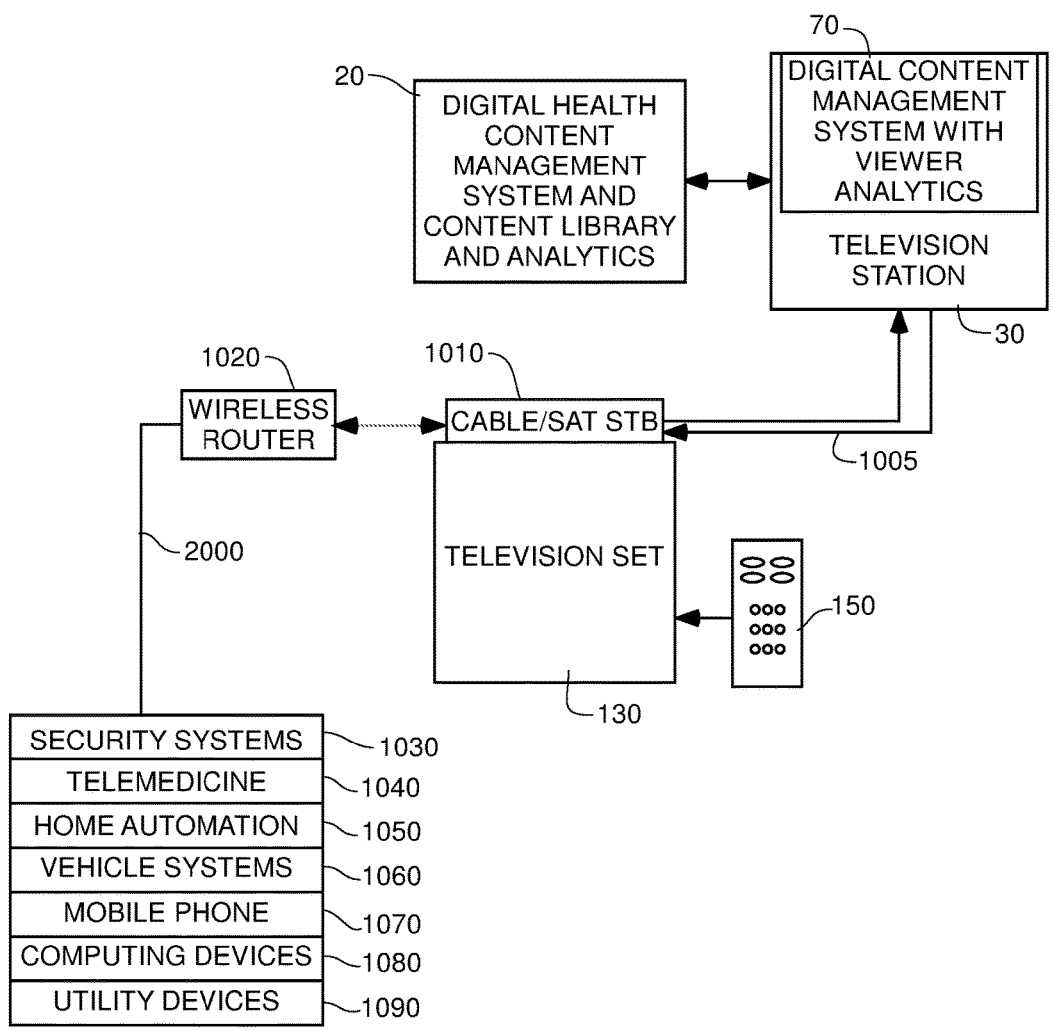
FIG. 12—Is a block diagram that illustrates the connectivity of a cable delivered television and Internet services with different wired or wireless household devices connected.

Turning now to FIG. 12, here a method is shown whereby the system 20 is configured to not only utilize existing television viewing analytics contained within CMS 70 (see FIG. 2) to optimize and customize delivery and understanding of health related digital content of database 200 but also utilize similar information types to generate repeatable patterns of daily activities from which certain conclusions can be drawn about a person's health or wellbeing. These methods are restricted to cable and satellite television systems 1010 that possess bidirectional 1005 communication back to the CMS 70 via a digital television set top box (DTSTB) rather than a digital broadcast set top converter box (DBSTCB). In the embodiment shown, much of the activity information generated will be performed by the patient/TV viewer 40 (see FIG. 1) utilizing the remote control 150 to turn the television set 130 on, off, or select different channels for viewing. In some embodiments, other patterns of activity data could be gathered from remote control or gesture-based television navigation devices (e.g. remote controls, etc.) since newer models have incorporated motion and accelerometers from which pieces of information can be extracted.

Though as mentioned above the various functions of the system 20 described thus far do not require the use of internet capable devices, in some embodiments the system 20 can be supplemented with additional inputs (and thus provide more/enhanced expanded analytic feedbacks or outputs) provided by internet capable systems. For example, as illustrated in FIG. 12, additional information about an individual viewer's daily activity levels could be gathered from measuring the amount of data passing through an Internet router 1020 that is operably connected to the cable or satellite set top box 1010. Other devices, either wired into or wirelessly connected also with cable or satellite set top box 1010, such as home security systems 1030, telemedicine devices 1040, home automation systems 1050, vehicle systems 1060, mobile telephones 1070, other conventional computing devices 1080, such as pc tablets and laptops, or even utility devices 1090 such as smart utility meters and thermostats could also provide valuable pieces of health, wellness, or activity information.

Figure 13:
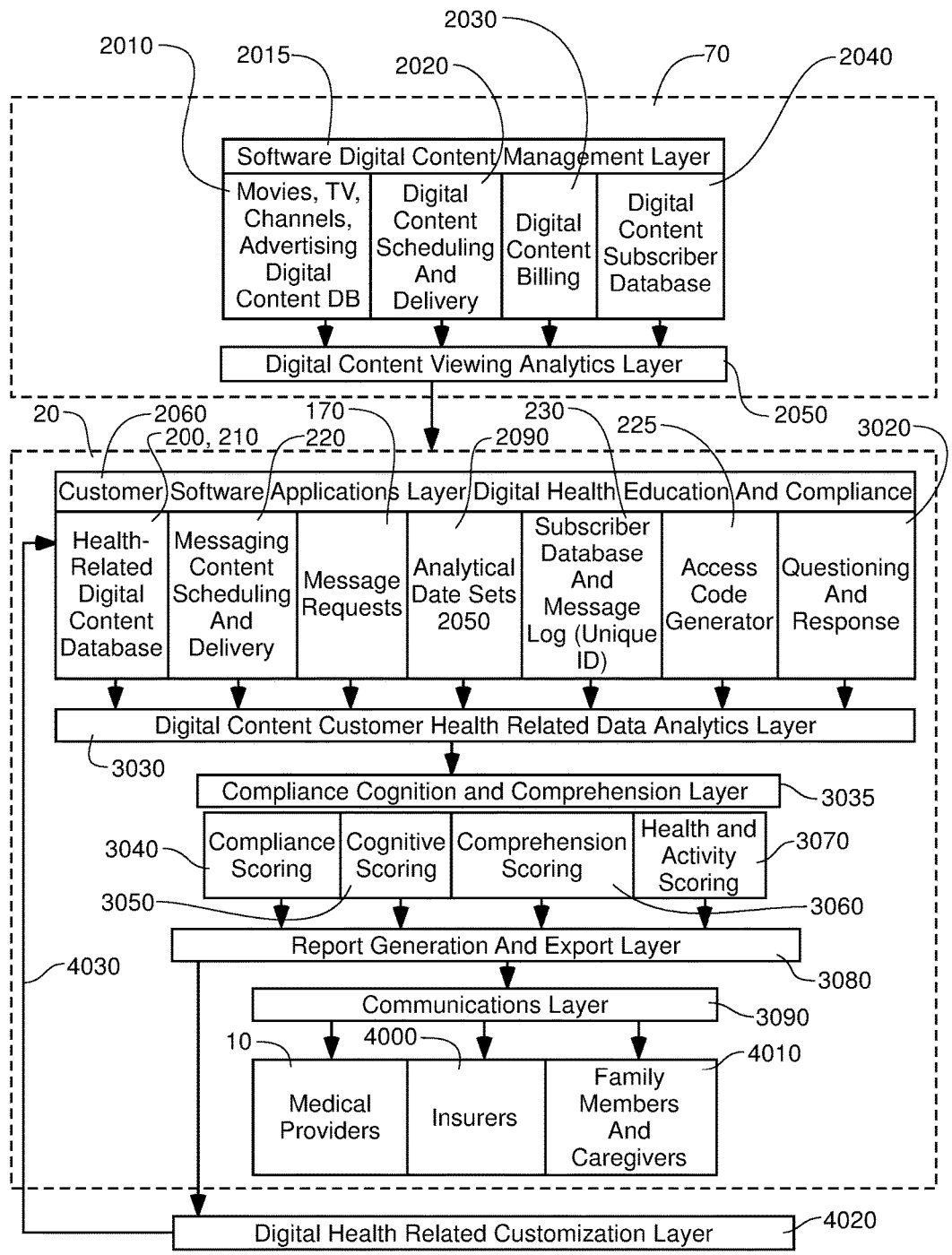
FIG. 13—Is a block diagram that illustrates the connectivity and electronic data exchange between a digital content management system and the system.

FIG. 13 illustrates a more comprehensive view of the data exchange method between the system of 20 and the content management system 70 of the digital television station 30 (see FIG. 1). Wherein the content management system 70 contains, but is not limited to a digital content entertainment storage database 2010, a scheduling system 2020, a billing system for purchased premium digital content 2030, and a database of subscribers 2040. Different data sets from within 2010, 2020, 2030, and 2040 can be extracted and combined into analytics table 2050 that provides more specific insights into a viewer's television viewing/activity patterns. The system 20 contains but is not limited to a database of health related digital content 200, a scheduling system 220 for when content (such as a video 210) is to be delivered, and the ability to electronically receive requests 160 to deliver the requested or scheduled content from database 200.

Additional aspects of system 20 include a message recipient database 230 that stores and tracks issuance of health related digital content delivery to a specific patient/TV viewer 40 (see FIG. 1) and individual access codes 225a that have been generated by 225 and assigned to specific patient/TV viewer 40 to access and view confidential health related digital content.

Another aspect of the system 20 includes a database of questions and recognized responses 3020 that can be associated and attached to delivery of digital health related content from database 200 to discover and record comprehension of delivered digital health related content; thereby providing a mechanism of adjustment to delivery of digital health related content to optimize its intent.

An additional layer residing within the system of 20 provides a scoring system based upon different data sets that have been analyzed via a digital content customer health-related data analytics layer/process 3030 from database 200, video content 210, scheduling element 220, digital content viewing analytics layer 2050 and questions and response database 3020 and categorized into the Compliance, Cognition, and Comprehension Layer 3035 that includes compliance scoring measures 3040, cognitive scoring measures 3050, comprehension scoring measures 3060, and health and activity scoring measures, 3070 from which summary reports are generated and electronically 3080 sent to the Communications Layer 3090 that include but is not limited to Medical Providers 10 but may also include: Insurers 4000, and Family members and caregivers 4010.

Scoring measures conducted within 3035 also provide important feedback for customizing digital health related content to align with scoring levels ascertained within the categories of: compliance scoring 3040, cognitive scoring 3050, comprehension scoring 3060 and health and activity scoring 3070. These data are electronically sent outside of the system of 20 to the digital health related customization layer 4020 where customization to the digital health related content occurs and then is sent and stored within the appropriate databases 200, 3020, within Customer Software Applications Layer 2060.

Figure 14:
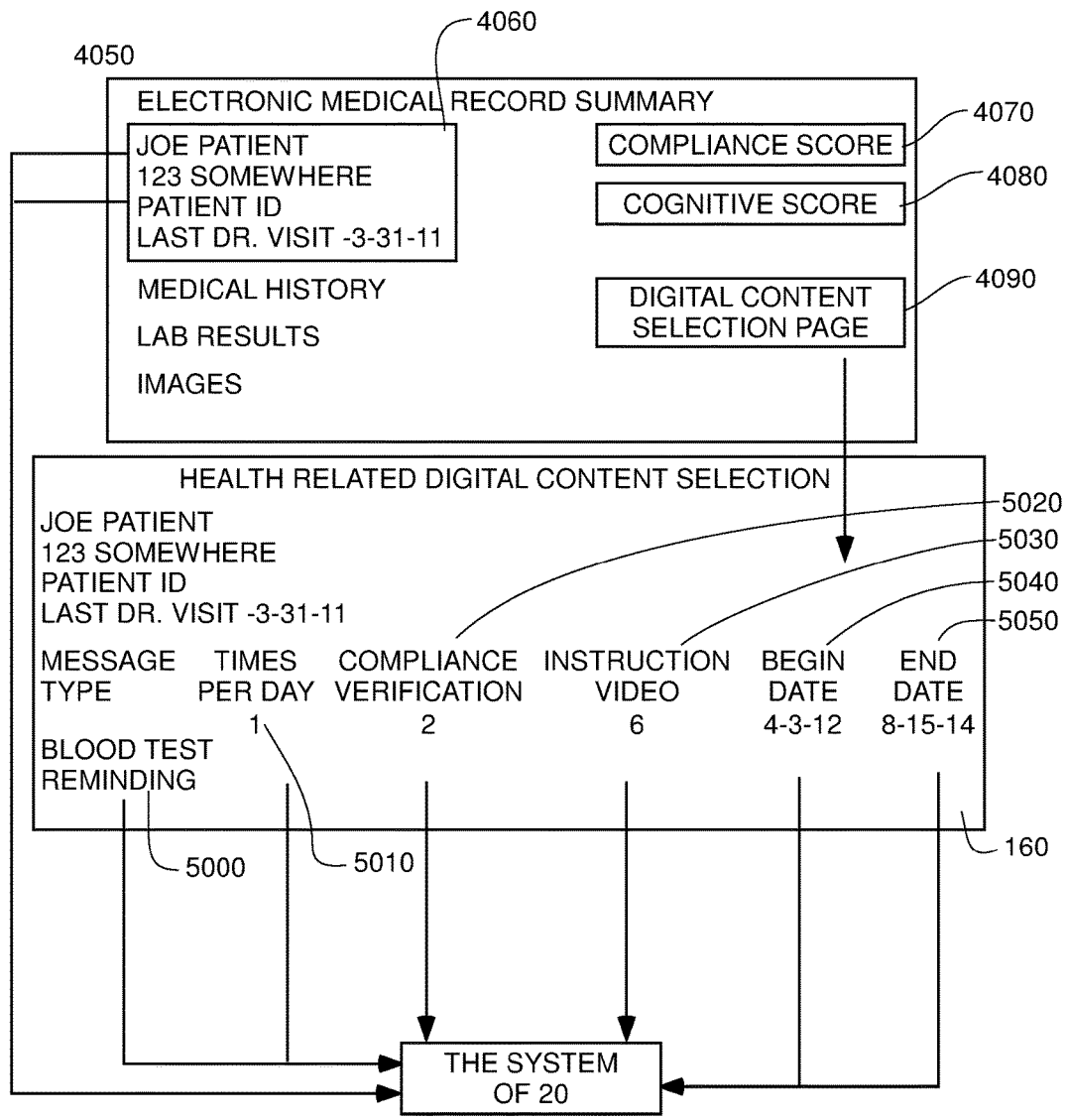
FIG. 14—Is a block diagram that illustrates how digital health-related content can be selected from an electronic medical record, delivered to a television set with different compliance metrics incorporated.

FIG. 14 illustrates the issuance of a request by a medical provider 10 utilizing an electronic medical record 4050 that stores all professionally administered medical activities of the patient/digital television viewer 40 to deliver digital health related content from database 200 (see FIG. 3). Digital content selection page 4090 is a visual embodiment within the electronic medical record 4050 that allows the medical provider 10 to select and send different types of health related digital content 4090 to a patient/digital television viewer 40. It is also contemplated that the digital health related content selection could become a highly automated process with digital health-related content being automatically selected based on several key factors, medical diagnosis, compliance score 4070 and cognition level. It is further contemplated that the cognition level could also be automatically assigned based on factors such as age and education levels.

Assisting the medical provider 10 on the type and format of health related digital content to select and send are visual compliance and cognitive scores embodiments, 4070 and 4080, also contained and displayed from within the electronic medical record 4050. The request message 160 coming from the medical provider 10 and to the system of 20 have only certain embodiments that must be used and merged with other pieces of data contained within the system of 20 and 70. The main information processing element 240 within the system of 20 will utilize certain data fields, name and address from 160 to search for the appropriate DAIC 340b of the digital television box 110, located within the CMS or a subscriber database located at the television station 30.

Within the electronic medical record 4050 is a medical content request area 4055 where the medical provider 10 is presented with various menus from which to select the type of digital health related message, frequency and the number of times per day 5010 digital health related message (presented in this examples as a reminder to conduct a blood test) 5000 should be delivered. In 5005, the medical provider 10 designated the confidential nature of the message to be sent, such as in the manner described above. In 5020 the medical provider 10 (see FIG. 1) is presented with selecting different methods to verify compliance 5020 to digital health related message 5000. As an additional reference to select the appropriate health related digital content the electronic medical record 4050 also displays a compliance 4070 and cognitive score 4080 that has been determined and updated from the system 20.

The medical provider 10 is also presented with the option of selecting a health related digital video 5030. The medical provider is presented with selecting a start date 5040 for delivery of health related digital content to begin and is also presented with entering a date 5050 for the delivery of health related digital content to discontinue. The selection process of 4055 may incorporate multiple digital health related message types, compliance verification and start/stop dates.

Formulation and selection of these digital health related message types will determined by assessment of medical provider 10 along with the unique health, cognitive abilities and compliancy levels of the patient/TV viewer 40.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

The invention claimed is:

1. A health-related digital content messaging and compliance system comprising:
a main processing element;
a health-related content database, the health-related content database containing health-related messages, the health-related content database configured to provide a health-related message with a digital address identification code;
a specific health-related content request database;
a patient personal medical information database;
a communication interface with a medical provider; and
a communication interface with a television station, the television station including a broadcast tower for transmitting a digital broadcast television signal wherein transmission of the digital broadcast television signal is coordinated by a content management system, the content management system being in electronic communication with the medical provider;
at least one television set, the television station in communication with at the least one television set through the digital broadcast television signal, the healthcare provider providing to the television station the health-related message, wherein the health-related message is in the form of a text message sent to the at least one television set by the content management system of the television station and within the digital broadcast signal of an unrelated television program, the at least one television set having a unique television digital address identification code, the health-related message is displayed on the at least one television set and concurrently with the unrelated television program only when the unique television digital address identification code of the at least one television set matches the digital address identification code of the health-related message;
the main processor constructed and arranged to facilitate communication and access of the health-related content database, the specific health-related content request database, the patient personal medical information database by at least one of the medical provider and the television station,
wherein the health-related message is a confidential message, and further comprising an individual access code generator constructed and arranged to provide the confidential message with an individual viewer access code, and
wherein after the confidential message is sent to the at least one television set by the television station the confidential message is displayed on the at least one television set only when the individual viewer access code of the confidential message matches a personal individual viewer access code input to the at least one television set by a viewer of the confidential message.

2. The system of claim 1 wherein the health-related messages consisting of: reminder messages, warning messages, miscellaneous information messages, educational messages, motivational messages, instructional messages and any combination thereof.

3. The system of claim 2 wherein the health-related message is requested by the medical provider via the communication link with the medical provider.

4. The system of claim 3 wherein the health-related message is sent to the television station via the communication link with the television station.

5. The system of claim 4 wherein the communication between the television station and the at least one television set is bidirectional.

6. The system of claim 5 further comprising a remote control in communication with the at least one television set upon which the health-related message is to be displayed, upon the display of the health-related message on the at least one television set, an acknowledgement of the health-related message can be input into the remote control and communicated back to the medical provider through the communication interface with the television station and the communication interface with the medical provider.

7. The system of claim 1 further comprising a remote control, the remote control in communication with the at least one television set upon which the confidential message is to be displayed, the personal individual viewer access code being input into the at least one television via the remote control.

8. The system of claim 7 wherein input from the remote control is recorded in the patient personal medical information database.

* * * * *